United States Patent [19]

Dillard, III et al.

[11] Patent Number: 5,057,086
[45] Date of Patent: Oct. 15, 1991

[54] SAFETY SYRINGE

[76] Inventors: John A. B. Dillard, III, 1640 Pierside La., Camarillo, Calif. 93010; James A. Orr, 7550 San Bari, Goleta, Calif. 93117

[21] Appl. No.: 559,836

[22] Filed: Jul. 30, 1990

[51] Int. Cl.⁵ .............................................. A61M 5/32
[52] U.S. Cl. .................. 604/195; 604/198; 604/263
[58] Field of Search .............. 604/187, 198, 263, 195, 604/136, 220

[56] References Cited

U.S. PATENT DOCUMENTS

| | | | |
|---|---|---|---|
| 4,820,275 | 4/1989 | Haber et al. | 604/198 |
| 4,932,940 | 6/1990 | Walker et al. | 604/110 |
| 4,932,947 | 6/1990 | Cardwell | 604/198 |
| 4,985,021 | 1/1991 | Straw et al. | 604/198 |

Primary Examiner—John D. Yasko
Attorney, Agent, or Firm—Harry W. Brelsford

[57] ABSTRACT

A tubular hypodermic needle syringe has a tubular sheath that slides over the exterior of the syringe to cover the needle. The sheath is locked over the needle by a latch that engages the syringe and the sheath. The latch is held in its locking engagement by a sliding collar that normally engages the latch to lock the latch but which is manually slidable to disengage the latch so that the sheath can be manually moved to expose the needle. A spring urges the collar to a latch engaging position to automatically lock the sheath over the needle.

12 Claims, 3 Drawing Sheets

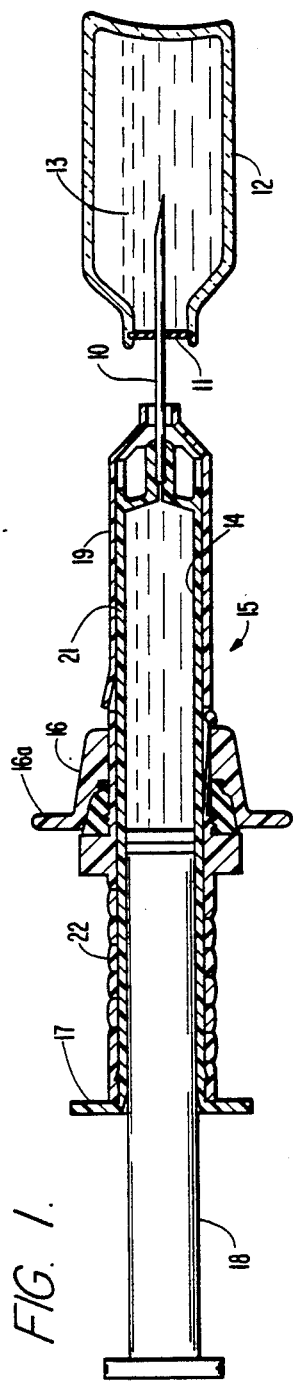
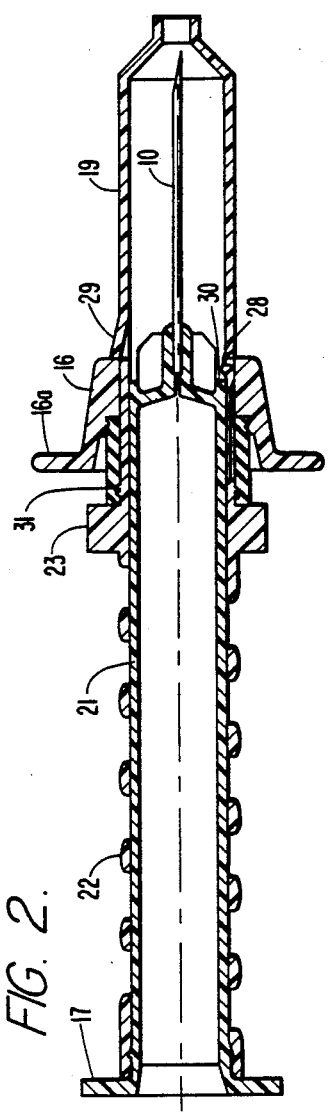
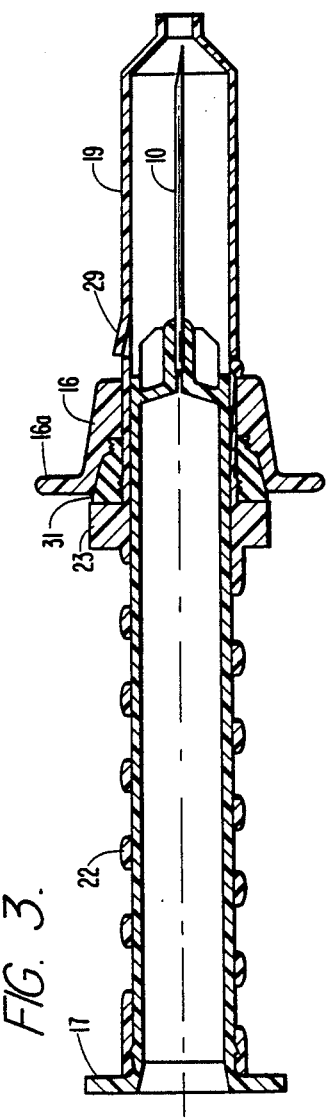

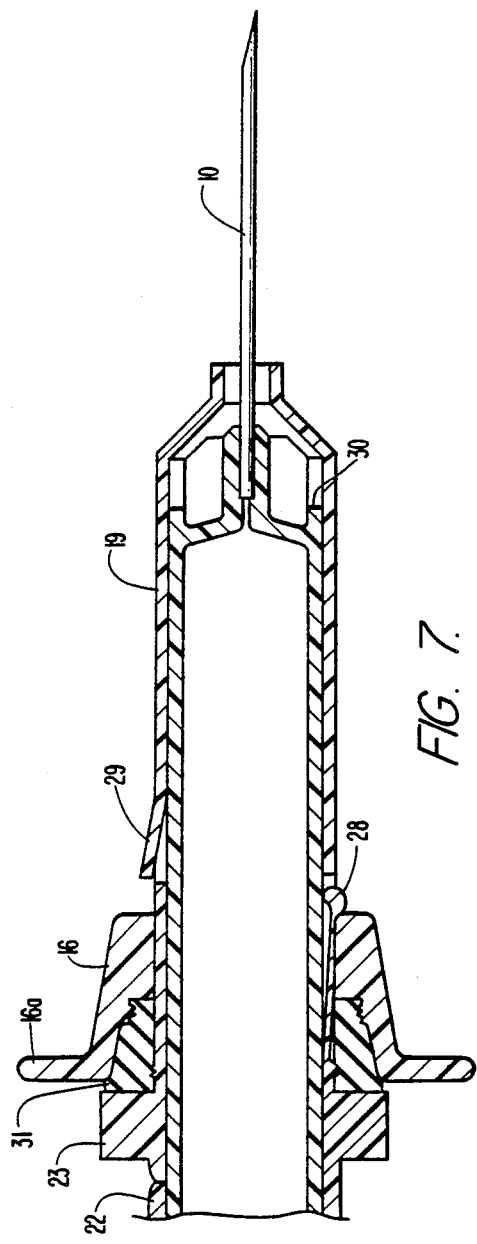
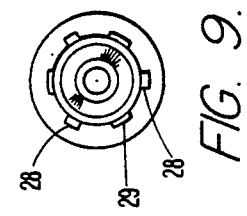
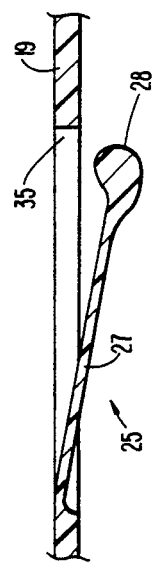
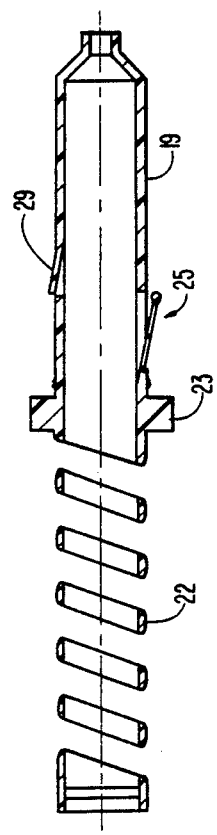

SAFETY SYRINGE

This invention relates to syringes for hypodermic needles and more particularly to an improved sliding protective needle cover mounted on the syringe to prevent accidental needle pricks.

BACKGROUND OF THE INVENTION

The advent of the AIDS virus requires that structures of the greatest safety be employed for hypodermic needle syringes. While blood extraction for diagnosis is an important area of hypodermic needle contamination, a much more frequent use of hypodermic needles occurs in the injection of medicine, anesthesia and various liquids. Once an injection is made and the needle withdrawn from the patient, the needle tip is contaminated with the microorganisms of the patient. Thereafter any accidental pricking of other persons by the needle will transfer to that person such microorganisms. Various removable sheaths have been devised to cover the needle both before and after use. However manually placing the sheath over the needle exposes the operator to accidental pricks of the needle. Various sliding sheaths have been devised that remain mechanically connected to the syringe at all times. Usually these sheaths are spring biased to cover the needle. However if the sheath contacts a person it will retreat and slide until the needle penetrates that person, passing on the contamination. The contamination is injected under the skin, an area where it cannot be easily removed and where the contamination is most likely to spread.

BRIEF DESCRIPTION OF THE INVENTION

The present invention provides a reciprocable sheath that is spring biased to normally cover the needle of a hypodermic syringe. The sheath is manually retracted against the push of the spring to uncover the needle. However, the sheath is locked in its protective position by latches. Therefore, if the syringe accidentally strikes a person, the sheath will contact that person and the needle will not make contact. Release is provided for the latches, and this release mechanism is presently preferred to be a sliding collar that is manually moved away from the needle point. Once the latches are released continued pulling on the collar also retracts the sheath to expose the needle point. The collar for releasing the latches is preferably urged toward the locking position by a spring that is independent of the spring that urges the sheath to cover the needle point. After the operator has finished using the syringe, the biasing spring returns the sheath over the needle. The spring on the sliding collar then locks the latches so that the sheath cannot retract or reciprocate.

Thereafter, even the most severe blows on the sheath will not move it. This is particularly important to persons who must remove waste and trash from a hospital or doctor's office. The rigidly positioned sheath will enable manual pickup of spent syringes if this proves to be necessary or desirable.

DESCRIPTION OF THE DRAWINGS

The drawings form an integral part of this specification and:

FIG. 1 is a sectional view of a hypodermic syringe embodying the invention while being used to extract a medicine or other therapeutic liquid from a bottle and transferring the liquid to the syringe interior.

FIG. 2 is a sectional view of the syringe body of FIG. 1 on an enlarged scale, showing a protective sheath overlying the needle.

FIG. 3 is a sectional view of the syringe FIG. 2 wherein the sliding collar has been manually moved to the left to release the latch mechanism.

FIGS. 5, 6 and 7 are enlarged parts in section of FIGS. 2, 3 and 4 respectively, to more clearly show the details of construction, and FIG. 7 is on a slightly reduced scale from FIGS. 5 & 6.

FIG. 8 is a sectional view of the one-piece construction of the sheath, latch and sheath spring.

FIG. 9 is an end view of the structure of FIG. 8 and

FIG. 10 is an enlarged sectional view of a portion of FIG. 8 showing the construction of the latch.

DETAILED DESCRIPTION OF THE DRAWINGS

Figure 4:
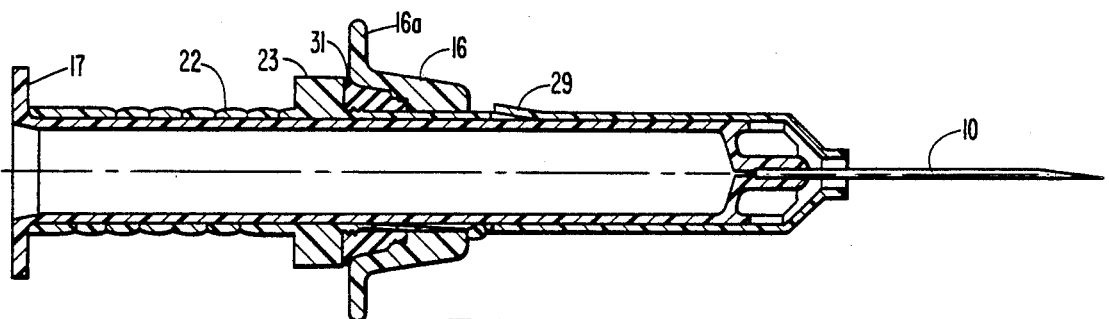
FIG. 4 is a sectional view of the syringe body of FIG. 2 wherein the protective sheath has been withdrawn to expose the needle for use.

Referring to FIG. 1 a hollow hypodermic needle 10 has pierced the rubber diaphragm 11 of a medicine bottle 12 and the liquid 13 is being withdrawn through the needle 10 and into the hollow interior 14 of a syringe 15. This transfer of liquid is accomplished by the operator holding a latch actuator collar 16 to the left by engaging the collar 16 with the fingers the syringe flange 17 with the thumb of one hand, while moving to the left a piston or plunger 18 with the fingers of the other hand.

When a sufficient amount of liquid has been withdrawn, the operator ceases pulling to the left on piston 18 and the needle is withdrawn from the bottle 12. The operator is now able to inject the liquid into a patient by inserting the needle 10 under the skin of the patient and pressing to the right on piston 18. After insertion of the liquid the needle is withdrawn from the patient. The needle is now contaminated and the needle is protected in accordance with the present invention by a sheath 19 which reciprocates on the exterior of a tubular syringe body 21 when the operator releases the manual pressure between collar 16 and syringe flange 17. A helical compression spring 22 also disposed on the exterior of the syringe body 21, now forces to the right the tubular sheath 19.

Referring now to FIGS. 8, 9 and 10 there is illustrated the one-piece construction of the helical spring 22, a collar stop flange 23 and the reciprocable sheath 19. This one-piece structure is presently preferred to be a molding of suitable plastic material, such as polycarbonate. Integrally molded as part of the one-piece construction is a latch 25 shown in detail in FIG. 10. The latch includes an arm 27 and a head 28. The latch arm 27 is molded at an angle from the tubular surface of the sheath 19 and therefore has a permanent set. This latch arm acts as a leaf spring to hold the latch head 28 radially outwardly as illustrated in FIG. 10. This molding avoids the use of an independent leaf spring to urge the latch head 28 radially outwardly. The latch arm 27 is elastic and allows the latch head to be moved into a slot 35 formed in the sheath 19. Shown in FIGS. 8 and 9 are integrally molded fingers 29 which act as a right hand stop for the actuating collar 16.

Figure 5:
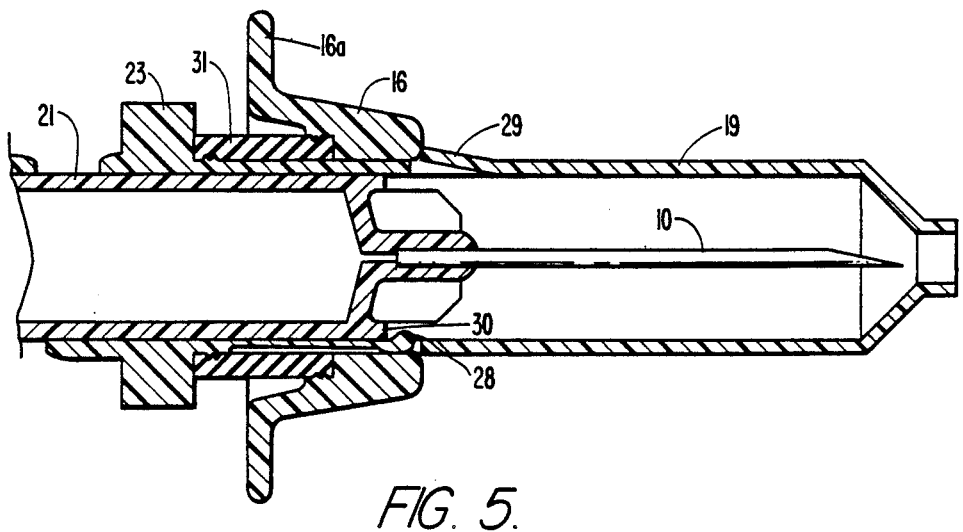

Referring now to FIGS. 2 through 7, the normal rest position of the parts is shown in FIGS. 2 & 5. Disposed over the sheath 19 is a rubber ring 31 which abuts against stop flange 23. This is preferably slipped over the right end of sheath 19. Also slipped over the right end of sheath 19 is the latch actuator collar 16 which depresses fingers 29 and when the collar 16 is moved past these fingers 29, they spring back to the position shown to act as the right hand stop for latch actuator 16. Actuator 16 preferably has a flange 16A to give an easier grip to the operator. If the sheath 19 of the structure of FIG. 2 is accidentally struck against a person or other object, the latch head 28 will be engaged by the right end 30 of syringe body 21 and the sheath will remain in place.

Figure 6:
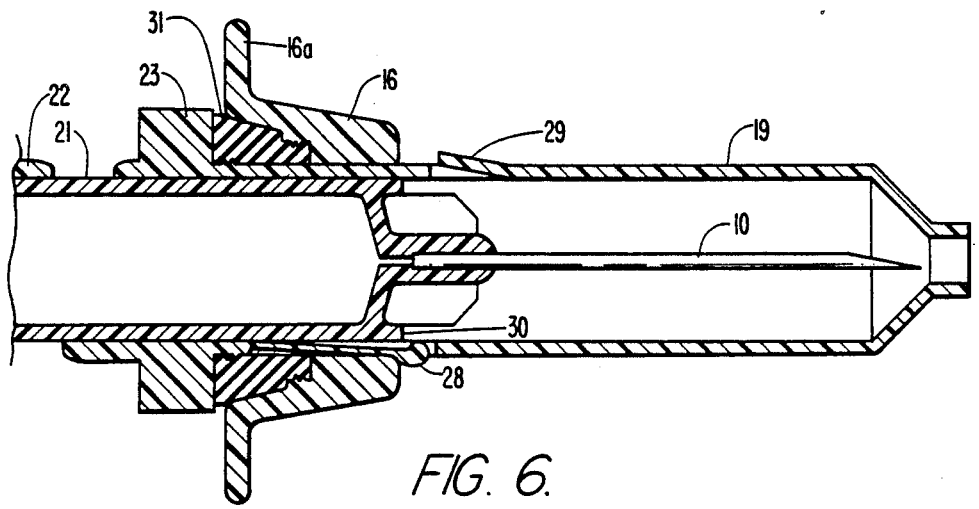

If it is now desired to expose the needle 10 to fill the syringe body 21 or inject a patient, the first step is shown in FIGS. 3 and 6. The operator engages the actuator flange 16A between two fingers while pressing with the thumb against syringe flange 17. This moves actuator collar 16 to the left which compresses rubber ring. 31. This movement of collar 16 to the left uncovers latch heads 28 and latch arms 27 of latches 25 and the build-in spring action of leaf 27 causes the latch heads 28 to move radially outwardly so that the right end 30 of syringe body 21 will no longer be engaged and the sheath 19 can be moved to the left.

The next step in exposing the needle is shown in FIGS. 4 and 7. The operator continues to move collar 16 to the left and this carries with it the sheath 19 because the stop flange 23 is part of the sheath 19. This movement compresses the helical spring 22 until it is entirely compressed as shown in FIG. 4. The needle 10 is now exposed for receiving liquid or injecting liquid into a patient.

If now the operator accidentally drops the syringe or places it on a shelf, the sheath spring 22 will move the sheath over the needle 10. At the same time the rubber ring will move actuator collar 16 to the right. This actuator movement forces latch heads 28 radially inwardly against the right end 30 of the syringe body 21. This position of parts is shown in FIG. 2. If a blow now is struck against the end of sheath the sheath will not move and will protect the needle point and protect any persons or objects coming in contact with the syringe.

OPERATION

The normal rest position of the syringe is shown in FIGS. 2 and 5. The sheath 19 covers the needle 10 and if a blow is struck against the right end of the sheath 19, it will not move with respect to the needle 10. This is due to latch head 28 interengaging the sheath 19 and the right end 30 of the syringe body 21. The needle point and any persons handling the syringe are fully protected.

To expose the needle for filling the syringe as shown in FIG. 1 or injecting liquid into a person, the operator grasps the flange 16A between two fingers and the syringe flange 17 with his thumb to move the actuator 16 to the left. This first movement compresses the rubber ring 31 as shown in FIGS. 3 and 6. This first movement of actuator 16 allows the latch heads 28 to move radially outwardly because of their build-in spring bias to move radially outwardly as shown in FIG. 10. This movement of latch heads 28 unlatches the sheath 19 from the syringe body 21, and the sheath 19 can now telescope over the syringe body 21.

The movement of the sheath 19 to uncover the needle 10 is shown in FIGS. 4 and 7. Further manual movement of latch operator collar 16 to the left brings with it the sheath 9 until the helical spring is fully compressed as shown in FIG. 4. The needle 10 is now fully exposed for loading the syringe with liquid as shown in FIG. 1 or injecting liquid into a patient. This is done by holding the syringe body between fingers and thumb of one hand while actuating the syringe piston 18 (FIG. 1) with the other hand. Injection may be accomplished with one hand by engaging the actuator 16 between fingers and the left end of piston 18 with the thumb.

MANUFACTURING DESIGN

The many hundreds of thousands of hypodermic syringes used daily requires the utmost in design simplicity, maximum production rates and minimum assembly operations. The present design achieves these objectives by the one-piece design of the spring, stop collar, latch fingers and sheath as shown in FIG. 8. Only three parts are assembled to achieve a combination that fits over common syringe designs. The assembly of the collar rubber ring 31 and the actuator 16 to the one-piece structure of FIG. 8 is easily accomplished by machine. The one-piece construction of FIG. 8 provides the spring action for the latch heads 28. The resilient fingers 29 provide an inexpensive right hand stop for actuator 16.

The invention has been described with respect to the presently preferred design as required by the patent statutes. Various modifications and changes will be apparent to those skilled in the art. All such variations, modifications, changes and improvements that come within the true spirit and scope of the invention are included within the scope of the attached claims. For example, after use a transverse nail or pin can be pushed or driven thru the extended sheath and the syringe body or through the sliding collar 16 to prevent any movement of the sheath.

We claim:

1. In combination with a hypodermic syringe having:
   (a) a hollow tubular syringe body,
   (b) a hollow needle communicating with the hollow of the syringe body,
   (c) a reciprocable tubular needle sheath disposed on the exterior of the syringe body, and
   (d) a spring engaging the syringe body and the sheath to urge the sheath to cover the needle, a latch mechanism to normally lock the sheath over the needle, and manually operable to unlock the sheath to expose the needle comprising:
   1) a latch engaging the sheath and the syringe body to lock the sheath over the needle:
   2) means for normally biasing the latch to a radially outward position to unlatch the sheath and syringe body;
   3) a latch actuator collar slidingly mounted on at least one of said sheath or the syringe body; and
   4) an actuator spring normally urging the collar to a position engaging the latch to hold the latch in engagement and to lock the sheath in a position over the needle, said actuator spring having a strength to be manually overcome to slide the actuator collar out of engagement with the latch.

2. The combination as set forth in claim 1 wherein the means for biasing the latch is a permanent elastic set in the latch itself.

3. The combination of claim 1 wherein the latch is carried by the sheath and the latch actuator collar is disposed on the exterior of the sheath.

4. The combination of claim 1 wherein a stop flange is connected to the sheath and the actuator spring is a ring of elastic material disposed between the stop flange and the latch actuator collar.

5. A sheath and latch for use with a tubular hypodermic syringe comprising:
   (a) a one-piece tubular sheath, latch collar stop and helical spring;
   (b) an annular spring disposed on the sheath having two edges with one edge at the collar stop; and
   (c) a latch actuator collar disposed over the sheath at the other edge of the annular spring and normally disposed over the latch.

6. The combination of claim 5 wherein the sheath is provided with resilient fingers to act as a stop for the latch actuator collar.

7. The combination of claim 5 wherein the latch has a built-in resilient position radially outwardly from the exterior of the sheath.

8. In the combination of a hypodermic syringe having:
   (a) a hollow body,
   (b) a hollow needle communicating with the body hollow,
   (c) a needle sheath reciprocable on the hollow body, and
   (d) a spring mounted on the syringe body and normally urging the sheath over the needle,
   a latch mechanism to normally lock the sheath over the needle, comprising:
   1) a latch interconnecting the hollow body and the sheath to hold the sheath over the needle;
   2) a manually operable sliding latch actuator mounted on the sheath; and
   3) a spring normally urging the latch actuator to a latching position to lock the sheath over the needle.

9. The structure as set forth in claim 8 wherein the latch is normally biased to an unlatching position.

10. The structure of claim 8 wherein the latch actuator is an external collar mounted on the sheath.

11. The structure of claim 8 wherein the latch is carried by the sheath.

12. In the combination of a hypodermic syringe having:
   (a) a hollow body,
   (b) a hollow needle communicating with the body hollow,
   (c) a needle sheath reciprocable on the hollow body, and
   a latch mechanism to normally lock the sheath over the needle, comprising:
   1) a latch interconnecting the hollow body and the sheath to hold the sheath over the needle;
   2) a manually operable sliding latch actuator mounted on the sheath; and
   3) a spring normally urging the latch actuator to a latching position to lock the sheath over the needle.

* * * * *